(12) United States Patent
Brock et al.

(10) Patent No.: US 9,693,940 B2
(45) Date of Patent: Jul. 4, 2017

(54) COSMETIC COMPOSITION COMPRISING A COLLAGEN PROTECTING OR ENHANCING AGENT AND PARTICLES COMPRISING SILICA AND TITANIUM DIOXIDE TOPICAL COMPOSITIONS

(71) Applicant: DSM IP ASSETS B. V., Heerlen (NL)

(72) Inventors: Achim Brock, Basel (CH); Christian Gstoettmayr, Basel (CH); Aline Hueber, Basel (CH); Szilvia Mesaros, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/890,738

(22) PCT Filed: May 14, 2014

(86) PCT No.: PCT/EP2014/059815
§ 371 (c)(1),
(2) Date: Nov. 12, 2015

(87) PCT Pub. No.: WO2014/184224
PCT Pub. Date: Nov. 20, 2014

(65) Prior Publication Data
US 2016/0081893 A1    Mar. 24, 2016

(30) Foreign Application Priority Data

May 16, 2013    (EP) .................................... 13168072

(51) Int. Cl.
| A61K 9/50 | (2006.01) |
| A61K 8/29 | (2006.01) |
| A61K 8/25 | (2006.01) |
| A61K 8/34 | (2006.01) |
| A61K 8/42 | (2006.01) |
| A61K 8/64 | (2006.01) |
| A61K 8/67 | (2006.01) |
| A61Q 19/08 | (2006.01) |
| A61K 8/02 | (2006.01) |
| A61K 8/06 | (2006.01) |
| A61K 8/58 | (2006.01) |
| A61K 8/66 | (2006.01) |
| A61K 8/97 | (2017.01) |
| A61Q 19/00 | (2006.01) |
| A61Q 19/02 | (2006.01) |

(52) U.S. Cl.
CPC .............. *A61K 8/29* (2013.01); *A61K 8/0283* (2013.01); *A61K 8/062* (2013.01); *A61K 8/25* (2013.01); *A61K 8/347* (2013.01); *A61K 8/42* (2013.01); *A61K 8/58* (2013.01); *A61K 8/64* (2013.01); *A61K 8/645* (2013.01); *A61K 8/66* (2013.01); *A61K 8/671* (2013.01); *A61K 8/673* (2013.01); *A61K 8/675* (2013.01); *A61K 8/676* (2013.01); *A61K 8/678* (2013.01); *A61K 8/97* (2013.01); *A61K 9/5026* (2013.01); *A61Q 19/00* (2013.01); *A61Q 19/02* (2013.01); *A61Q 19/08* (2013.01); *A61K 2800/412* (2013.01); *A61K 2800/413* (2013.01); *A61K 2800/592* (2013.01); *C12Y 115/01001* (2013.01)

(58) Field of Classification Search
CPC .............................. A61K 9/5026; A61Q 19/08
See application file for complete search history.

(56) References Cited

U.S. PATENT DOCUMENTS

| 2007/0065396 A1* | 3/2007 | Morariu .................. A61K 8/14 424/74 |
| 2008/0188574 A1* | 8/2008 | Lee ..................... B01F 17/0021 516/79 |
| 2009/0175915 A1 | 7/2009 | Maitra et al. |

FOREIGN PATENT DOCUMENTS

| EP | 0 988 853 | * 3/2000 |
| KR | 2008-0038622 | 5/2008 |
| WO | WO 95/09598 | 4/1995 |
| WO | WO 2007/065574 | 6/2007 |
| WO | WO 2011/061133 | 5/2011 |
| WO | WO 2012/104160 | 8/2012 |

OTHER PUBLICATIONS

International Search Report for PCT/EP2014/059815 mailed Jul. 30, 2014, four pages.
Solving Skin Problems, Misbn Jul. 5335-1863-2, Marshal Editions Developments Ltd., London Uk (1999).

* cited by examiner

*Primary Examiner* — Carlos Azpuru
(74) *Attorney, Agent, or Firm* — Nixon & Vanderhye P.C.

(57) ABSTRACT

The present invention relates to a topical composition comprising at least one collagen protecting and/or collagen enhancing agent and a silica-titanium dioxide composite particle having a particle size $D_v0$ of greater 0.3 µm, a $D_v100$ of less than 35 µm and a $D_v50$ of 4.0 to 10 µm, wherein the silica-titanium dioxide composite particle consists of 20-45 wt.-% titanium dioxide particles having a particle size $D_v50$ of 100 to 300 nm embedded in a matrix of silica. Furthermore the invention relates to the use of such silica-titanium dioxide composite particles to ameliorate the sensory properties of a topical composition comprising collagen protecting agent and/or collagen enhancing agent as well as to reduce the short and long term eye contour puffiness, dark eye circles, crow's feet and fine lines.

11 Claims, No Drawings

COSMETIC COMPOSITION COMPRISING A COLLAGEN PROTECTING OR ENHANCING AGENT AND PARTICLES COMPRISING SILICA AND TITANIUM DIOXIDE TOPICAL COMPOSITIONS

This application is the U.S. national phase of International Application No. PCT/EP2014/059815 filed 14 May 2014 which designated the U.S. and claims priority to EP Patent Application No. 13168072.0 filed 16 May 2013, the entire contents of each of which are hereby incorporated by reference.

The present invention relates to a topical composition comprising at least one collagen protecting and/or collagen enhancing agent and a silica-titanium dioxide composite particle having a particle size $D_v0$ of greater 0.3 μm, a $D_v100$ of less than 35 μm and a $D_v50$ of 4.0 to 10 μm, wherein the silica-titanium dioxide composite particle consists of 20-45 wt.-% titanium dioxide particles having a particle size $D_v50$ of 100 to 300 nm embedded in a matrix of silica. Furthermore the invention relates to the use of such silica-titanium dioxide composite particles to ameliorate the sensory properties of a topical composition comprising collagen protecting agent and/or collagen enhancing agent as well as to reduce the short and long term eye contour puffiness, dark eye circles, crow's feet and fine lines.

Fatigue, sun damage and skin aging may all cause dark circles and under-eye bags to develop, dulling the appearance of the eye contour area.

Thus, there is an ongoing demand for topical compositions which conceal shadows and dark circle that dull the appearance and still look natural of the eye and provide a short and long term 'rested and revitalized' look.

Furthermore, there is an ongoing need to further improve the complex sensory properties of topical compositions in order to fulfill all of the demanding expectations on the part of the end consumers which is economical.

Surprisingly it has been found that the addition of relatively low amounts of a specific silica-titanium dioxide composite particle to a topical composition comprising at least one collagen protecting and/or collagen enhancing agent significantly improves the sensory properties as well as provides instant reduction of eye contour puffiness, dark circles, crow's feet and fine lines.

Thus, the present invention relates to a topical composition comprising at least one collagen protecting and/or collagen enhancing agent, characterized in that the composition further comprises a silica-titanium dioxide composite particle having a particle size $D_v0$ of greater 0.3 μm, a $D_v100$ of less than 35 μm and a $D_v50$ of 2.0 to 10 μm, wherein the silica-titanium dioxide composite particle consists of 20-45 wt.-% of titanium dioxide particles having a particle size $D_v50$ of 100 to 300 nm embedded in a matrix of silica.

Another subject matter of the invention is directed to the use of a silica-titanium dioxide composite particle having a particle size $D_v0$ of greater 0.3 μm, a $D_v100$ of less than 35 μm and a $D_v50$ of 2.0 to 10 μm, wherein the silica-titanium dioxide composite particle consists of 20-45 wt.-% of titanium dioxide particles having a particle size $D_v50$ of 100 to 300 nm embedded in a matrix of silica in combination with at least one collagen protecting and/or collagen enhancing agent to refine the short and long term eye contour appearance and/or to improve the sensory properties. Preferably, the topical compositions according to the present invention are used for immediate and long term reduction of eye contour puffiness, dark circles, crow's feet and fine lines.

Furthermore, the invention is directed to a method for improving the immediate and long term eye contour appearance and/or the sensory properties said method comprising applying to the skin a topical composition comprising at least one collagen protecting and/or collagen enhancing agent, characterized in that the topical composition further comprises a silica-titanium dioxide composite particle having a particle size $D_v0$ of greater 0.3 μm, a $D_v100$ of less than 35 μm and a $D_v50$ of 2.0 to 10 μm, wherein the silica-titanium dioxide composite particle consists of 20-45 wt.-% titanium dioxide particles having a particle size $D_v50$ of 100 to 300 nm embedded in a matrix of silica and appreciating the effect. Preferably, the method is used for short and long term reduction of eye contour puffiness, dark circles, crow's feet and fine lines.

Preferably, the improved sensory properties are an increased waxiness and a reduced gloss and greasiness resulting in an overall more velvet skin feel.

In all embodiments of the present invention preferably the amount of the silica-titanium dioxide particle is selected in the range of 0.1 to 5 wt.-% such as in the range of 1-5 wt.-% such as most preferably in the range of 2 to 4 wt.-% based on the total weight of the cosmetic composition.

Preferably in all embodiments of the present invention the particle size $D_v50$ of the silica-titanium dioxide particle is selected in the range of 2.5 to 8 μm such as most preferably in the range selected of 3 to 6 μm.

Furthermore, in all embodiments of the present invention the particle size $D_v50$ of the titanium dioxide particles is selected in the range of 150 to 250 nm. Most preferably the particle size $D_v50$ of the titanium dioxide particles is in the range of 200 to 250 nm.

It is furthermore advantageous if the amount of the titanium dioxide particles within the silica matrix is selected in the range of 25-40 wt.-% such as most preferably in the range of 27 to 35 wt.-% based on the total weight of the silica-titanium dioxide composite particle. It is understood that in all embodiments of the present invention the amount of the titanium dioxide particles and the silica matrix in the silica-titanium dioxide particle sum up to 100 wt.-%.

The crystalline form of the titanium dioxide may be of any crystal or amorphous type. For example, titanium dioxide may be any type of amorphous, rutil, anatase, brookite or a mixture thereof. Preferably, the crystalline form of the titanium dioxide in the silica-titanium dioxide particles according to the present invention is rutil.

The refractive index (calculated) of the silica-titanium dioxide composite particle according to the present invention is preferably smaller than 2. More preferably, the refractive index is selected in the range of 1.5 to 1.9 and most preferably in the range of 1.7-1.8. The refractive index of the silica-titanium dioxide composite particle according to the present invention can easily be adjusted by a person skilled in the art by modifying the ratio of titanium dioxide particles to silica matrix.

The term 'a collagen enhancing/protecting agent' as used herein refers to any active agent which stimulates collagen synthesis and/or protects collagen from degradation. Preferred collagen enhancing and/or protecting agents encompass Vitamin C (ascorbic acid) as well as derivatives thereof, retinol, polypeptides such as more preferably peptides with 2 to 5 amino acids or collagen synthesis stimulating or collagen protecting plant extracts as well as mixtures thereof.

The amount of the collagen enhancing and/or protecting agent can easily be adjusted by a person in the art. Preferably the amount of the collagen enhancing and/or protecting agent is—independently of each other—selected in the range of 0.01-10 wt.-%, more preferably in the range of 0.1 to 5 wt.-%, and most preferably in the range of 0.5 to 3 wt.-% based on the total weight of the composition. It is understood that the given amounts are based on the respective product as commercially available and not to the actual active ingredient within the respective product form.

Particular suitable Vitamin C derivatives to be used in the topical compositions according to the present invention are sodium ascorbyl phosphate which is commercially available as Stay-C® 50 at DSM Nutritional Products Ltd.

Further particular suitable collagen enhancing and/or protecting agents to be used in the topical compositions according to the present invention are the peptides (INCI names) Palmitoyl Tripeptide-5 (e.g. commercially available under the trade name SYN®-COLL at DSM Nutritional Products Ltd), Palmitoyl Tetrapeptide-7 (e.g. commercially available as Matrixyl® 3000 at Sederma); Acetyl Tetrapeptide-9 (e.g. commercially available as Dermican™ LS 9745 at Laboratoires Serobiologiques/Cognis). Particularly suitable in all embodiments according to the present invention is the use of Palmitoyl Tripeptide-5 as it stimulates collagen synthesis as well as protects collagen from degradation.

Particularly suitable collagen synthesis stimulating plant extracts to be used in the topical compositions according to the present invention are *Pisum Sativum* Extract e.g. commercially available under the trade name Proteasyl® TP LS 8657, Proteasyl® LS 8951 or Proteasyl® LS 9818 at BASF, *Vigna Aconitifolia* Extract e.g. commercially available under the trade name Vit-A-Like™ LS 9793 or Vit-A-Like™ LS 9898 at BASF as well as *Hibiscus abelmoschus* seed extract e.g. commercially available as Linefactor™ at BASF.

Further preferred collagen protecting agents encompass natural rice and soy peptides and biotechnologically produced superoxide dismutase. Such agents are e.g. commercially available as REGU®-AGE PF at DSM Nutritional Products Ltd.

Particular preferred collagen protecting and enhancing agents are peptides with 2 to 5 amino acids as they have a dual action in stimulating the synthesis and inhibiting degradation of collagen. Most preferred under this aspect in all embodiments of the present invention is the use of Palmitoyl Tripeptide-5.

It is furthermore particularly preferred to combine Palmitoyl Tripeptide-5, natural rice and soy peptides and biotechnologically produced superoxide dismutase e.g. by using the combination of SYN®-COLL and REGU®-AGE PF.

The particle size (in volume %) as given in the present invention is determined by a Coulter LS13320 or Malvern Mastersizer 2000 according to standard methods in the art.

The silica-titanium dioxide composite particles according to the present invention are preferably obtained by embedding the titanium dioxide in a matrix of silica which is obtainable by common methods in the art such as e.g. polymerization of sodium silicate (also known as water glass) in the presence of an acid or a base.

Suitable titanium dioxide particles to be embedded into the silica matrix are e.g. commercially available as Titanium Dioxide CR-50 at Ishihara Sangyo Kaisha Ltd.

The particle form of the composite particles in all embodiments of the present invention is preferably spherical, and in such a case, the particle size represents the diameter.

Particularly suitable silica-titanium dioxide composite particle according to the present invention have a particle size $D_v0$ of greater 0.3 µm, a $D_v100$ of less than 35 µm and a $D_v50$ of 3 to 6 µm, wherein the silica-titanium dioxide composite particle consists of 27 to 35 wt.-% of titanium dioxide particles having a particle size $D_v50$ of 200 to 250 nm embedded in a matrix of silica. Furthermore, it is preferred that the crystalline form of the titanium dioxide particles is rutil. It is furthermore advantageous if the composite particles exhibit as 10% aqueous dispersion in distilled water a pH in the range of 5.0-9.0.

Suitable silica-titanium dioxide composite particles according to the present invention are e.g. commercially available as VALVANCE™ Look 100 at DSM Nutritional Products Ltd Kaiseraugst.

The term "topical" is understood here to mean external application to keratinous substances, which are in particular the skin, scalp, eyelashes, eyebrows, nails, mucous membranes and hair.

As the compositions according to the invention are intended for topical application, they comprise a physiologically acceptable medium, that is to say a medium compatible with keratinous substances, such as the skin, mucous membranes, and keratinous fibers. In particular the physiologically acceptable medium is a cosmetically acceptable carrier.

The term cosmetically acceptable carrier refers to all carriers and/or excipients and/or diluents conventionally used in cosmetic compositions.

Preferred topical compositions according to the invention are skin care preparations or functional preparations.

Examples of skin care preparations are, in particular, light protective preparations (sunscreens), anti-ageing preparations, preparations for the treatment of photo-ageing, body oils, body milks, body lotions, body gels, treatment creams, skin protection ointments, skin powders, moisturizing creams, moisturizing gels, moisturizing sprays, face and/or body moisturizers, skin-tanning preparations (i.e. compositions for the artificial/sunless tanning and/or browning of human skin), for example self-tanning creams as well as skin lightening preparations, foundations and functional foundations such as BB and CC Creams.

Examples of functional preparations are cosmetic or pharmaceutical compositions containing active ingredients such as hormone preparations, vitamin preparations, vegetable and/or plant extract preparations, anti-ageing preparations, and/or antimicrobial (antibacterial or antifungal) preparations without being limited thereto.

In a particular embodiment the topical compositions according to the invention are skin care preparations, such as (body) milks, lotions, hydrodispersions, foundations, creams, creamgels, serums, toners or gels.

The topical compositions according to the present invention may be in the form of a suspension or dispersion in solvents or fatty substances, or alternatively in the form of an emulsion or micro emulsion (in particular of oil-in-water (O/W-) or water-in-oil (W/O-)type, silicone-in-water (Si/W-) or water-in-silicone (W/Si-)type, PIT-emulsion, multiple emulsion (e.g. oil-in-water-in oil (O/W/O-) or water-in-oil-in-water (W/O/W-)type), pickering emulsion, hydrogel, alcoholic gel, lipogel, one- or multiphase solution or vesicular dispersion or other usual forms, which can also be applied by pens, as masks or as sprays.

In one embodiment, the topical compositions according to the present invention are advantageously in the form of an oil-in-water (O/W) emulsion comprising an oily phase dispersed in an aqueous phase in the presence of an O/W emulsifier. The preparation of such O/W emulsions is well known to a person skilled in the art and illustrated in the examples.

If the topical composition according to the invention is an O/W emulsion, then it contains advantageously at least one O/W- or Si/W-emulsifier selected from the list of PEG-30 Dipolyhydroxystearate, PEG-4 Dilaurate, PEG-8 Dioleate, PEG-40 Sorbitan Peroleate, PEG-7 Glyceryl Cocoate, PEG-20 Almond Glycerides, PEG-25 Hydrogenated Castor Oil, Glyceryl Stearate (and) PEG-100 Stearate, PEG-7 Olivate, PEG-8 Oleate, PEG-8 Laurate, PEG-60 Almond Glycerides, PEG-20 Methyl Glucose Sesquistearate, PEG-40 Stearate, PEG-100 Stearate, PEG-80 Sorbitan Laurate, Steareth-2, Steareth-12, Oleth-2, Ceteth-2, Laureth-4, Oleth-10, Oleth-10/Polyoxyl 10 Oleyl Ether, Ceteth-10, Isosteareth-20, Ceteareth-20, Oleth-20, Steareth-20, Steareth-21, Ceteth-20, Isoceteth-20, Laureth-23, Steareth-100, Glyceryl Stearate Citrate, Glyceryl Stearate SE (self-emulsifying), stearic acid, salts of stearic acid, polyglyceryl-3-methylglycosedistearate. Further suitable emulsifiers are phosphate esters and the salts thereof such as cetyl phosphate (Amphisol® A), diethanolamine cetyl phosphate (Amphisol®DEA), potassium cetyl phosphate (Amphisol® K), sodiumcetearylsulfat, sodium glyceryl oleate phosphate, hydrogenated vegetable glycerides phosphate and mixtures thereof. Further suitable emulsifiers are sorbitan oleate, sorbitan sesquioleate, sorbitan isostearate, sorbitan trioleate, Cetearyl Glucoside, Lauryl Glucoside, Decyl Glucoside, Sodium Stearoyl Glutamate, Sucrose Polystearate and Hydrated Polyisobuten. Furthermore, one or more synthetic polymers may be used as an emulsifier. For example, PVP eicosene copolymer, acrylates/$C_{10-30}$ alkyl acrylate crosspolymer, acrylates/steareth-20 methacrylate copolymer, PEG-22/dodecyl glycol copolymer, PEG-45/dodecyl glycol copolymer, and mixtures thereof.

The at least one O/W respectively Si/W emulsifier is preferably used in an amount of 0.2 to 10 wt.-%, in particular in the range of 0.5 to 6 wt.-% such as more in particular in the range of 0.5 to 5 wt.-% such as most in particular in the range of 1 to 4 wt.-%, based on the total weight of the topical composition.

Particular suitable O/W emulsifiers according to the present invention encompass phosphate esters emulsifier of formula (II)

formula (II)

wherein $R^5$, $R^6$ and $R^7$ may be hydrogen, an alkyl of from 1 to 22 carbons, preferably from 12 to 18 carbons; or an alkoxylated alkyl having 1 to 22 carbons, preferably from 12 to 18 carbons, and having 1 or more, preferably from 2 to 25, most preferably 2 to 12, moles ethylene oxide, with the provision that at least one of $R^5$, $R^6$ and $R^7$ is an alkyl or alkoxylated alkyl as previously defined but having at least 6 alkyl carbons in said alkyl or alkoxylated alkyl group.

Monoesters in which $R^5$ and $R^6$ are hydrogen and $R^7$ is selected from alkyl groups of 10 to 18 carbons and alkoxylated fatty alcohols of 10 to 18 carbons and 2 to 12 moles ethylene oxide are preferred. Among the preferred phosphate ester emulsifier are $C_{8-10}$ Alkyl Ethyl Phosphate, $C_{9-15}$ Alkyl Phosphate, Ceteareth-2 Phosphate, Ceteareth-5 Phosphate, Ceteth-8 Phosphate, Ceteth-10 Phosphate, Cetyl Phosphate, C6-10 Pareth-4 Phosphate, $C_{12-15}$ Pareth-2 Phosphate, $C_{12-15}$ Pareth-3 Phosphate, DEA-Ceteareth-2 Phosphate, DEA-Cetyl Phosphate, DEA-Oleth-3 Phosphate, Potassium cetyl phosphate, Deceth-4 Phosphate, Deceth-6 Phosphate and Trilaureth-4 Phosphate. A particular advantageous phosphate ester emulsifier according to the invention is potassium cetyl phosphate e.g. commercially available as Amphisol® K at DSM Nutritional Products Ltd. Kaiseraugst.

Further suitable O/W emulsifiers are polyethyleneglycol (PEG) esters or diesters such as e.g. [INCI Names] PEG-100 Stearate, PEG-30 Dipolyhydroxystearate, PEG-4 Dilaurate, PEG-8 Dioleate, PEG-40 Sorbitan Peroleate, PEG-7 Glyceryl Cocoate, PEG-20 Almond Glycerides, PEG-25 Hydrogenated Castor Oil, PEG-7 Olivate, PEG-8 Oleate, PEG-8 Laurate, PEG-60 Almond Glycerides, PEG-20 Methyl Glucose Sesquistearate, PEG-40 Stearate, PEG-100 Stearate, PEG-80 Sorbitan Laurate.

Particularly preferred according to the present invention is PEG-100 Stearate sold under the tradename Arlacel™ 165 (INCI Glyceryl Stearate (and) PEG-100 Stearate) by Croda.

Another particular suitable class of O/W emulsifiers are non-ionic self-emulsifying system derived from olive oil e.g. known as (INCI Name) cetearyl olivate and sorbitan olivate (Chemical Composition: sorbitan ester and cetearyl ester of olive oil fatty acids) sold under the tradename OLIVEM 1000.

In particular embodiment, the invention relates to topical compositions in the form of O/W emulsions comprising an oily phase dispersed in an aqueous phase in the presence of an O/W emulsifier wherein the O/W emulsifier is selected from the group consisting of potassium cetyl phosphate, glyceryl stearate (and) PEG-100 Stearate, cetearyl olivate and sorbitan olivate as well as mixtures thereof.

In another particular embodiment, the invention relates to topical compositions in the form of W/O emulsions comprising water dispersed in an oily phase in the presence of a W/O emulsifier.

Particularly suitable W/O emulsifiers are polyglycerol esters or diesters of fatty acids also called polyglyceryl ester/diester (i.e. a polymer in which fatty acid(s) is/are bound by esterification with polyglycerine), such as e.g. commercially available at Evonik as Isolan GPS [INCI Name Polyglyceryl-4 Diisostearate/Polyhydroxystearate/Sebacate (i.e. diester of a mixture of isostearic, polyhydroxystearic and sebacic acids with Polyglycerin-4)] or Dehymuls PGPH available at Cognis (INCI Polyglyceryl-2 Dipolyhydroxystearate). Particularly preferred according to the püresent invention are W/O emulsions wherein the W/O emulsifier is Polyglyceryl-3 Diisostearate.

The topical compositions according to the present invention furthermore advantageously contain at least one co-surfactant such as e.g. selected from the group of mono- and diglycerides and/or fatty alcohols. The co-surfactant is generally used in an amount selected in the range of 0.1 to 10 wt.-%, such as in particular in the range of 0.5 to 5 wt.-%, such as most in particular in the range of 1 to 3 wt.-%, based on the total weight of the composition. Particular suitable co-surfactants are selected from the list of alkyl alcohols such as cetyl alcohol (Lorol C16, Lanette 16) cetearyl alcohol (Lanette O), stearyl alcohol (Lanette 18), behenyl alcohol (Lanette 22), glyceryl stearate, glyceryl myristate (Estol 3650), hydrogenated coco-glycerides (Lipocire Na10) as well as mixtures thereof.

The compositions in form of O/W or W/O emulsions according to the invention can be provided, for example, in all the formulation forms for cosmetic emulsions, for example in the form of serum, milk or cream, and they are prepared according to the usual methods. The compositions which are subject-matters of the invention are intended for topical application and can in particular constitute a dermatological or cosmetic composition, for example intended for protecting human skin against the adverse effects of UV radiation (antiwrinkle, anti-ageing, moisturizing, anti-sun protection and the like).

According to an advantageous embodiment of the invention the compositions constitute cosmetic composition and are intended for topical application to the skin.

In accordance with the present invention, the compositions according to the invention may comprise further ingredients such as ingredients for skin lightening; tanning prevention; treatment of hyperpigmentation; preventing or reducing acne, wrinkles, lines, atrophy and/or inflammation; chelators and/or sequestrants; anti-cellulites and slimming (e.g. phytanic acid), firming, moisturizing and energizing, self-tanning, soothing, as well as agents to improve elasticity and skin barrier and/or further UV-filter substances and carriers and/or excipients or diluents conventionally used in topical compositions. If nothing else is stated, the excipients, additives, diluents, etc. mentioned in the following are suitable for topical compositions according to the present invention. The necessary amounts of the cosmetic and dermatological adjuvants and additives can, based on the desired product, easily be determined by the skilled person. The additional ingredients can either be added to the oily phase, the aqueous phase or separately as deemed appropriate. The mode of addition can easily be adapted by a person skilled in the art.

The cosmetically active ingredients useful herein can in some instances provide more than one benefit or operate via more than one mode of action.

The topical cosmetic compositions of the invention can also contain usual cosmetic adjuvants and additives, such as preservatives/antioxidants, fatty substances/oils, water, organic solvents, silicones, thickeners, softeners, emulsifiers, sunscreens, antifoaming agents, moisturizers, aesthetic components such as fragrances, surfactants, fillers, sequestering agents, anionic, cationic, nonionic or amphoteric polymers or mixtures thereof, propellants, acidifying or basifying agents, dyes, colorings/colorants, abrasives, absorbents, essential oils, skin sensates, astringents, antifoaming agents, pigments or nanopigments, e.g. those suited for providing a photoprotective effect by physically blocking out ultraviolet radiation, or any other ingredients usually formulated into such compositions. Such cosmetic ingredients commonly used in the skin care industry, which are suitable for use in the compositions of the present invention are e.g. described in the International Cosmetic Ingredient Dictionary & Handbook by Personal Care Product Council (http://www.personalcarecouncil.org/), accessible by the online INFO BASE (http://online.personalcarecouncil.org/jsp/Home.jsp), without being limited thereto.

The necessary amounts of the cosmetic and dermatological adjuvants and additives can—based on the desired product—easily be chosen by a skilled person in this field and will be illustrated in the examples, without being limited hereto.

Of course, one skilled in this art will take care to select the above mentioned optional additional compound or compounds and/or their amounts such that the advantageous properties intrinsically associated with the combination in accordance with the invention are not, or not substantially, detrimentally affected by the envisaged addition or additions.

The topical compositions according to the invention in general have a pH in the range of 3 to 10, preferably a pH in the range of 4 to 8 and most preferably a pH in the range of 4 to 7.5. The pH can easily be adjusted as desired with suitable acids such as e.g. citric acid or bases such as Sodium Hydroxide (aqueous solution), Triethanolamine (TEA Care), Tromethamine (Trizma Base) and Aminomethyl Propanol (AMP-Ultra PC 2000) according to standard methods in the art.

The amount of the topical composition to be applied to the skin is not critical and can easily be adjusted by a person skilled in the art. Preferably the amount is selected in the range of 0.1-3 mg/cm$^2$ skin, such as preferably in the range of 0.1-2 mg/cm$^2$ skin, and most preferably in the range of 0.5-2 mg/cm$^2$ skin.

The following examples are provided to further illustrate the compositions and effects of the present invention. These examples are illustrative only and are not intended to limit the scope of the invention in any way.

EXAMPLE

TABLE 1

| | | | A | B | Control |
|---|---|---|---|---|---|
| | | Formulation | | | |
| | Ingredient | INCI name | % w/w | | |
| A | Amphisol ® K | Potassium Cetyl phosphate | 1.0 | 1.0 | 1.0 |
| | Lanette 16 | Cetyl Alcohol | 3.0 | 3.0 | 3.0 |
| | Cutina CP | Cetyl Palmitate | 1.5 | 1.5 | 1.5 |
| | Eutanol G | Octyldodecanol | 3.0 | 3.0 | 3.0 |
| | Cetiol SN | Cetearyl Isononanoate | 2.5 | 2.5 | 2.5 |
| | Pemulen TR-1 | Acrylate/C10-30 Alkyl Acrylate Crosspolymer | 0.10 | 0.10 | 0.10 |
| | Valvance ™ Look 100$^\Delta$ | Silica (and) Titanium Dioxide | 3.0 | | |
| | SH219* | Silica (and) Titanium Dioxide | | 5.0 | |
| B | Glycerin 99.5% AMI | Glycerin PH. EUR. Vegetable | 3.0 | 3.0 | 3.0 |
| | Water dem. | Aqua | | | Ad 100 |

TABLE 1-continued

| | | Formulation | | | |
|---|---|---|---|---|---|
| | | | A | B | Control |
| Ingredient | INCI name | | | % w/w | |
| C Regu ®-Age PF | Glycine Soja Protein, Hydrolyzed Rice Extract, Superoxide Dismutase, Glycerin, Aqua, Phenoxyethanol, Sodium Benzoate, Potassium Sorbate, Sodium Dextran Sulfate | | 3.0 | 3.0 | 3.0 |
| SYN ®-COLL | Palmitoyl Tripeptide-5, Glycerin, Aqua | | 1.0 | 1.0 | 1.0 |
| Euxyl PE 9010 | Phenoxyethanol, Ethylhexylglycerin | | 0.8 | 0.8 | 0.8 |

$^A$Valvance™ Look 100 (DSM Nutritional Products Ltd): Silica-titanium dioxide composite particles having a particle size $D_v0$ of greater 0.3 μm, a $D_v100$ of less than 35 μm, a $D_v50$ of 3 to 6 μm, a titanium dioxide content of 28-32 wt.-% and a titanium dioxide particle size of about 200 nm.
*SH219 (Sunjin Chemicals Ltd): Silica-titanium dioxide composite particles having a (silica) bead size of 5 μm, a titanium dioxide content of 25 wt.-% and a titanium dioxide particle size of 12 nm.

Preparation:
1. Heat phase A and B separately to 80° C.
2. Add phase B to A while stirring, homogenize for 1 min.
3. Cool down to RT, add phase C and homogenize again.

Sensory Evaluation

The sample A (Inventive) and B (Reference) prepared as outlined above were tested in a blind study with a trained sensorial panel consisting of 6 persons under the following conditions:

The evaluation takes part on the inner forearm; the panel leader applies 50 μL of the respective sample.

Evaluator spreads the product within a defined circle of 5 cm diameter using index or middle finger, circular motion, rate of 2 rotations/second. This is the so called rub-out phase. After the rub-out phase the sensory properties were assessed according to standardized parameters. The intensities felt are quantified on a scale from 0 to 100 in comparison to training standards with known and defined sensory intensities.

TABLE 1

Results of the sensory evaluation

| | Gloss | Greasy | Waxy |
|---|---|---|---|
| Formulation B (Reference) | 17 | 7 | 70 |
| Formulation A (Inventive) | 14 | 5 | 75 |
| Δ (value A − value B) * 100%/value B | −18% | −29% | +7% |

Gloss: Amount of light reflected off skin (untreated skin=10), absolute value
Greasy: Percentage of perceived greasy character (solid, fatty) of the residue
Waxy: Percentage of perceived waxy character (dry, dull) of the residue A reduced gloss, a reduced greasiness and an increased waxiness results in an overall more dry and velvet skin feel. Thus, as can be retrieved the silica-titanium dioxide composite particles according to the present invention result in a more pronounced overall velvet skin feel compared to the reference.

Furthermore, formulation A was tested against placebo in a blind study with 12 female volunteers in a half side study. Formulation A was applied on one side of the face, the placebo on the other side. The ITA° was determined against non-treated skin and skin treated with the placebo after 120 min.

The skin was evaluated by colorimetric parameters (Δ ITA°) against skin treated with placebo, respectively non-treated (initial). The results are presented in table 2.

TABLE 2

| Δ ITA° versus placebo | Δ ITA° versus non-treated |
|---|---|
| 5.58 | 7.06 |

As can be retrieved from the results the addition of 3% of Valvance™ Look 100 leads to a significant increase of the ITA° parameter by 5.48 (+78%) versus placebo and by 7.06 (+81.7%) versus the non-treated area.

Formulation Examples

Intensive O/W Cream

| Phase | Ingredients | INCI Name | % w/w |
|---|---|---|---|
| A | WATER DEM. | AQUA | ad 100 |
| | Glycerin 86.5% | GLYCERIN | 5.0 |
| | SYN ®-COLL | PALMITOYL TRIPEPTIDE-5, GLYCERIN, AQUA | 2.5 |
| B | Crodafos CES | CETEARYL ALCOHOL, DICETYL PHOSPHATE, CETETH-10 PHOSPHATE | 5.0 |
| | Myritol 331 | COCOGLYCERIDES | 6.0 |
| | Tegosoft TN | C12-15 ALKYL BENZOATE | 3.0 |
| | Tegosoft DC | DECYL COCOATE | 3.0 |
| | Fitoderm ® | SQUALANE | 2.0 |
| C | Natriumhydroxid 10% Lösung | SODIUM HYDROXIDE, AQUA | q.s. |
| D | Dow Corning 345 Fluid | CYCLOPENTASILOXAN (AND) CYCLOHEXASILOXAN | 3.0 |
| | Euxyl K 300 | PHENOXYETHANOL, METHYLPARABEN, BUTYLPARABEN, ETHYLPARABEN, PROPYLPARABEN, ISOBUTYLPARABEN | 0.8 |

-continued

| Phase | Ingredients | INCI Name | % w/w |
|---|---|---|---|
| | Aristoflex AVC | AMMONIUM ACRYLOYLDIMETHYLTAURATE/VP COPOLYMER | 0.4 |
| F | Transcutol CG | ETHOXYDIGLYCOL | 5.0 |
| G | VALVANCE ™ Look 100 | SILICA (AND) TITANIUM DIOXIDE | 5.0 |

10
Clarifying Perfection Cream

| Phase | Ingredients | INCI Name | % w/w |
|---|---|---|---|
| A | Estol 3650 | GLYCERYL MYRISTATE | 1.5 |
| | Lanette 16 | CETYL ALCOHOL | 1.5 |
| | Finsolv TN | C12-15 ALKYL BENZOATE | 4.0 |
| | Phenonip | PHENOXYETHANOL, METHYLPARABEN, ETHYLPARABEN, BUTYLPARABEN, PROPYLPARABEN, ISOBUTYLPARABEN | q.s. |
| | Lanol 99 | ISONONYL ISONONANOATE | 2.0 |
| | Brij 72 | STEARETH-2 | 1.5 |
| | Brij 721 | STEARETH-21 | 1.5 |
| B | Keltrol CG-T | XANTHAN GUM | 0.3 |
| | Carbopol Ultrez 21 | ACRYLATES/C10-30 ALKYL ACRYLATE CROSSPOLYMER | 0.25 |
| C | 1,3-Butylenglycol | BUTYLENE GLYCOL | 2.0 |
| | Glycerin 86.5% | GLYCERIN | 3.0 |
| | Edeta BD | DISODIUM EDTA | 0.1 |
| | WATER DEM. | AQUA | ad 100 |
| D | WATER DEM. | AQUA | 10.05 |
| | STAY C ® 50 | SODIUM ASCORBYL PHOSPHATE | 2.0 |
| | Salicylic acid | SALICYLIC ACID | 0.6 |
| E | Potassium Hydroxide 30% sol. | POTASSIUM HYDROXIDE | 0.75 |
| F | VALVANCE ™ Look 100 | SILICA (AND) TITANIUM DIOXIDE | 3.5 |

35
Improved Look Cream

| Phase | Ingredients | INCI Name | % w/w |
|---|---|---|---|
| A | Estol 3650 | GLYCERYL MYRISTATE | 1.5 |
| | Lanette 16 | CETYL ALCOHOL | 1.5 |
| | Finsolv TN | C12-15 ALKYL BENZOATE | 4.0 |
| | Phenonip | PHENOXYETHANOL, METHYLPARABEN, ETHYLPARABEN, BUTYLPARABEN, PROPYLPARABEN, ISOBUTYLPARABEN | q.s. |
| | Lanol 99 | ISONONYL ISONONANOATE | 2.0 |
| | Brij 72 | STEARETH-2 | 1.5 |
| | Brij 721 | STEARETH-21 | 1.5 |
| | VALVANCE ™ Look 100 | SILICA (AND) TITANIUM DIOXIDE | 4.0 |
| B | 1,3-Butylenglycol | BUTYLENE GLYCOL | 2.0 |
| | Glycerin 86.5% | GLYCERIN | 3.0 |
| | Edeta BD | DISODIUM EDTA | 0.1 |
| | Keltrol CG-T | XANTHAN GUM | 0.3 |
| | Carbopol Ultrez 21 | ACRYLATES/C10-30 ALKYL ACRYLATE CROSSPOLYMER | 0.25 |
| | WATER DEM. | AQUA | ad 100 |
| C | WATER DEM. | AQUA | 10.0 |
| | STAY C ® 50 | SODIUM ASCORBYL PHOSPHATE | 3.0 |
| | Natriumdisulfit | SODIUM METABISULFITE | 0.05 |
| D | Citric Acid, Anhydrous | CITRIC ACID | 0.5 |

Snow White Skin Lightening Cream

| Phase | Ingredients | INCI Name | % w/w |
|---|---|---|---|
| A | Estol 3609 | TRIETHYLHEXANOIN | 4.0 |
|   | Cetiol C5 | COCO-CAPRYLATE | 5.0 |
|   | Lanette 16 | CETYL ALCOHOL | 2.0 |
|   | Brij 72 | STEARETH-2 | 2.0 |
|   | Brij 721 | STEARETH-21 | 2.0 |
|   | Dow Corning 345 Fluid | CYCLOPENTASILOXAN (AND) CYCLOHEXASILOXAN | 3.0 |
|   | Finsolv TN | C12-15 ALKYL BENZOATE | 5.0 |
|   | MIXED TOCOPHEROLS 95 | TOCOPHEROL | 0.05 |
| B | Glycerin 86.5% | GLYCERIN | 4.0 |
|   | Edeta BD | DISODIUM EDTA | 0.1 |
|   | WATER DEM. | AQUA | ad 100 |
| C | NIACINAMIDE ®PC | NIACINAMIDE | 4.4 |
|   | STAY C ® 50 | SODIUM ASCORBYL PHOSPHATE | 1.0 |
|   | D-BIOTIN | BIOTIN | 0.1 |
|   | WATER DEM. | AQUA | 10.0 |
| D | Euxyl PE 9010 | PHENOXYETHANOL, ETHYLHEXYLGLYCERIN | q.s. |
|   | VALVANCE ™ Look 100 | SILICA (AND) TITANIUM DIOXIDE | 2.5 |

Skin Tone Corrector

| Phase | Ingredients | INCI Name | % w/w |
|---|---|---|---|
| A | Imwitor 372 P | GLYCERYL STEARATE CITRATE | 2.0 |
|   | Lanette 16 | CETYL ALCOHOL | 1.0 |
|   | Lipocire Na 10 Pastilles | HYDROGENATED COCO-GLYCERIDES | 1.0 |
|   | Finsolv TN | C12-15 ALKYL BENZOATE | 4.0 |
|   | Dow Corning 200 Fluid 100 CST | DIMETHICONE | 2.0 |
|   | Tegosoft M | ISOPROPYL MYRISTATE | 6.0 |
|   | DL-ALPHA-TOCOPHERYL ACETAT | TOCOPHERYL ACETATE | 0.2 |
| B | Keltrol CG-T | XANTHAN GUM | 0.15 |
|   | Pemulen TR-1 | ACRYLATES/C10-30 ALKYL ACRYLATE CROSSPOLYMER | 0.3 |
|   | WATER DEM. | AQUA | ad 100 |
| C | REGU ®-FADE | RESVERATROL | 1.0 |
|   | Dow Corning 190 Surfactant | PEG/PPG-18/18 DIMETHICONE | 4.0 |
|   | 1,2-Propandiol | PROPYLENE GLYCOL | 5.0 |
| D | Euxyl PE 9010 | PHENOXYETHANOL, ETHYLHEXYLGLYCERIN | q.s. |
|   | Natriumhydroxid 30% Lösung | AQUA, SODIUM HYDROXIDE | 0.3 |
| E | VALVANCE ™ Look 100 | SILICA (AND) TITANIUM DIOXIDE | 3.0 |

Multi-Active Brightening Cream

| Phase | Ingredients | INCI Name | % w/w |
|---|---|---|---|
| A | Myritol 318 | CAPRYLIC/CAPRIC TRIGLYCERIDE | 5.0 |
|   | Isopropyl Myristate | ISOPROPYL MYRISTATE | 2.0 |
|   | Fitoderm ® | SQUALANE | 1.5 |
|   | Phenonip | PHENOXYETHANOL, METHYLPARABEN, ETHYLPARABEN, BUTYLPARABEN, PROPYLPARABEN, ISOBUTYLPARABEN | q.s. |
| B | D-PANTHENOL 75% | PANTHENOL, AQUA | 2.0 |
|   | Novemer EC-1 Polymer | ACRYLATES/ACRYLAMIDE COPOLYMER, POLYSORBATE 85 | 1.0 |
|   | Carbopol Ultrez 21 | ACRYLATES/C10-30 ALKYL ACRYLATE CROSSPOLYMER | 0.2 |
|   | WATER DEM. | AQUA | ad 100 |
| C | REGU ®-FADE | RESVERATROL | 0.1 |
|   | Eumulgin HRE 40 | PEG-40 HYDROGENATED CASTOR OIL | 1.0 |
| D | Triethanolamine Care | TRIETHANOLAMINE | 0.2 |

-continued

| Phase | Ingredients | INCI Name | % w/w |
|---|---|---|---|
| E | SYN®-COLL | Palmitoyl Tripeptide-5, Glycerin, Aqua | 1.5 |
| F | VALVANCE™ Look 100 | SILICA (AND) TITANIUM DIOXIDE | 3.5 |

The invention claimed is:

1. A method for improving short and long term eye contour appearance, the method comprising applying to skin of an individual in need of improved eye contour appearance an effective amount of a topical composition and appreciating the improved eye contour effect, wherein the topical composition comprises:
   at least one collagen protecting and/or collagen enhancing agent selected from the group consisting of Vitamin C and derivatives thereof, retinol, polypeptides, collagen synthesis stimulating plant extract and collagen protecting plant extracts, and
   silica-titanium dioxide composite particles having a particle size $D_v0$ of greater 0.3 μm, a $D_v100$ of less than 35 μm and a $D_v50$ of 2.0 to 10 μm, wherein the silica-titanium dioxide composite particles consist of 20-45 wt.-% titanium dioxide particles having a particle size $D_v50$ of 100 to 300 nm embedded in a matrix of silica.

2. The method according to claim 1, wherein the silica-titanium dioxide composite particles are present in the topical composition in an amount within a range of 0.1-5 wt.-% based on the total weight of the composition.

3. The method according to claim 1, wherein the particle size $D_v50$ of the silica-titanium dioxide composite particles is in a range of 3 to 6 μm, the particle size $D_v50$ of the titanium dioxide particles is in a range of 200-250 nm and the amount of titanium dioxide particles embedded in the matrix of silica is in a range of 27-35 wt. %.

4. The method according to claim 1, wherein the silica-titanium dioxide composite particles have a refractive index of less than 2.

5. The method according to claim 4, wherein the refractive index of the silica-titanium dioxide composite particles is in a range of 1.5 to 1.9.

6. The method according to claim 1, wherein the collagen enhancing and/or protecting agent is at least one selected from the group consisting of sodium ascorbyl phosphate, polypeptides with 2 to 5 amino acids, natural rice, soy peptides and biotechnologically produced superoxide dismutase.

7. The method according to claim 1, wherein the collagen enhancing and/or protecting agent is at least one selected from the group consisting of palmitoyl tripeptide 5, natural rice and soy peptides and biotechnologically produced superoxide dismutase.

8. The method according to claim 1, wherein the amount of the collagen enhancing and/or protecting agent are independently of each other present in the topical composition in an amount in a range 0.01-10 wt. %, based on the total weight of the composition.

9. The method according to claim 1, wherein the topical composition is in the form of an O/W emulsion comprising an oily phase dispersed in an aqueous phase in the presence of an O/W emulsifier.

10. The method according to claim 9, wherein the O/W emulsifier is potassium cetyl phosphate.

11. The method according to claim 9, wherein the O/W emulsifier is present in an amount in a range of 1 to 4 wt. %, based on the total weight of the composition.

* * * * *